United States Patent [19]
Ansorge et al.

[11] Patent Number: 5,912,118
[45] Date of Patent: Jun. 15, 1999

[54] METHOD FOR SEQUENCING NUCLEIC ACIDS

[75] Inventors: Wilhelm Ansorge; Hartmut Voss, both of Gaiberg, Germany

[73] Assignee: Europaisches Laboratorium fur Molekularbiologie (EMBL), Germany

[21] Appl. No.: 08/182,173

[22] PCT Filed: Aug. 3, 1992

[86] PCT No.: PCT/EP92/01756

§ 371 Date: Apr. 18, 1994

§ 102(e) Date: Apr. 18, 1994

[87] PCT Pub. No.: WO93/03180

PCT Pub. Date: Feb. 18, 1993

[30] Foreign Application Priority Data

Aug. 2, 1991 [DE] Germany .............................. 41 25 745
Apr. 29, 1992 [DE] Germany .............................. 42 14 112

[51] Int. Cl.$^6$ .............................. C12Q 1/68; C12P 19/34
[52] U.S. Cl. ........................... 435/6; 435/91.1; 435/91.2; 435/91.5; 436/94
[58] Field of Search .................... 435/6, 91.2, 94, 435/91.5, 91.1; 536/26.6; 935/77, 78; 436/94

[56] References Cited

U.S. PATENT DOCUMENTS

| | | | |
|---|---|---|---|
| 4,795,699 | 1/1989 | Innis | 435/5 |
| 5,124,247 | 6/1992 | Ansorge | 435/6 |
| 5,674,679 | 10/1997 | Fuller | 435/6 |

FOREIGN PATENT DOCUMENTS

| | | |
|---|---|---|
| 0371437 | 6/1990 | European Pat. Off. . |
| 3839397 | 5/1990 | Germany . |
| 3841565 | 6/1990 | Germany . |
| 9004645 | 5/1990 | WIPO . |

OTHER PUBLICATIONS

Brumbaugh et al. Proceedings of the National Academy of Sciences. 85:5610–5614, Aug. 1988.
Prober et al. Science. 238:336–341, Oct. 1987.
Sanger et al., Proc. Natl. Acad. Sci. 74(12):5463–5467, Dec. 1977.
Maxam et al., Proc. Natl. Acad. Sci. 74(2):560–564, Feb. 1977.

*Primary Examiner*—Carla J. Myers
*Attorney, Agent, or Firm*—Nikaido Marmelstein Murray & Oram, LLP

[57] ABSTRACT

In order to sequence nucleic acids one produces a mixture of labelled nucleic acid fragments of different length, using nucleic acid fragments which are labelled by incorporation of at least one deoxyribonucleoside triphosphate with a non-radioactive labelling group, separates the labelled nucleic acid fragments according to size and determines the nucleic acid sequence by means of the labelling of the individual fragments.

19 Claims, 5 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 360 base pairs
        (B) TYPE: nucleic acid
        (C) STRANDEDNESS: single
        (D) TOPOLOGY: circular (ii) MOLECULE TYPE: DNA (ix) FEATURE:
        (A) NAME/KEY: misc_feature
        (B) LOCATION: 22
        (D) OTHER INFORMATION: /note= "N is an unidentified
            nucleotide"

(ix) FEATURE:
        (A) NAME/KEY: misc_feature
        (B) LOCATION: 23
        (D) OTHER INFORMATION: /note= "N is an unidentified
            nucleotide"

(ix) FEATURE:
        (A) NAME/KEY: misc_feature
        (B) LOCATION: 24
        (D) OTHER INFORMATION: /note= "N is an unidentified
            nucleotide"

(ix) FEATURE:
        (A) NAME/KEY: misc_feature
        (B) LOCATION: 25
        (D) OTHER INFORMATION: /note= "N is an unidentified
            nucleotide"

(xi) SEQUENCE DESCRIPTION: SEQ ID NO:1:

```
CGGCCATGGA ATTGTAATAC GNNNNCTATA GGGCGAATTG GCCAAGTCGG CCGAGCTCGA      60

ATTCGTCGAC CTCGAGGGAT CCGGGCCCTC TAGATGCGGC CGCATGCATA AGCTTGAGTA     120

TTCTATAGTG TCACCTAAAT AGCTTGGCGT AATCATGGTC ATAGCTGTTT CCTGTGTGAA     180

ATTGTTATCC GCTCACAATT CCACACAACA TACGAGCCGG AAGCATAAAG TGTAAAGCCT     240

GGGGTGCCTA ATGAGTGAGC TAACTCACAT TAATTGCGTT GCGCTCACTG CCCGCTTTCC     300

AGTCGGGAAA CCTGTCGTGC CAGCTGCATT AATGAATTCG GCCAACGCGC GGGGAGAGGC     360
```

(2) INFORMATION FOR SEQ ID NO:2:

(i) SEQUENCE CHARACTERISTICS:
        (A) LENGTH: 231 base pairs
        (B) TYPE: nucleic acid
        (C) STRANDEDNESS: single
        (D) TOPOLOGY: circular (ii) MOLECULE TYPE: DNA (xi) SEQUENCE DESCRIPTION: SEQ ID NO:2:

```
CCTATATCAC ATATTGAGGA GTAAAAATGT CATATCTTTT AAAAGTATTT TATTCTATGC      60

CTGTATATAG AAGAAATTGT GAAGTACATA ACTAGAGGAA AGTTACTGTT AAAAGTGGAG     120

AATACCTAAG TTGTCTAATA CGAGAAAGGT TTTTATTTAA TTTTTTCACA CATACACAAC     180

TCTGATTAGT GCTATAAGTT ACATTGTGGT GTTCATGTAT TTCAATGTAT T              231
```

(2) INFORMATION FOR SEQ ID NO:3:

(i) SEQUENCE CHARACTERISTICS:
        (A) LENGTH: 953 base pairs
        (B) TYPE: nucleic acid
        (C) STRANDEDNESS: single
        (D) TOPOLOGY: circular (ii) MOLECULE TYPE: DNA (ix) FEATURE:
        (A) NAME/KEY: misc_feature
        (B) LOCATION: 54
        (D) OTHER INFORMATION: /note= "N is an unidentified
            nucleotide"

(ix) FEATURE:
        (A) NAME/KEY: misc_feature
        (B) LOCATION: 920
        (D) OTHER INFORMATION: /note= "N is an unidentified
            nucleotide"

(ix) FEATURE:
        (A) NAME/KEY: misc_feature
        (B) LOCATION: 921
        (D) OTHER INFORMATION: /note= "N is an unidentified
            nucleotide"

(xi) SEQUENCE DESCRIPTION: SEQ ID NO:3:

```
TCTTGTAATT TAGTGAAGTG AACGACTACC GATTTCATTA TTGGCTTGGA TATNTGAGGT      60

AAAACTTCAT TTCTGTTTAT ATAGTGCTGA CTTTCATTTG AAATTTAACG GATGGTAACT     120

TGCTGCCTCA AGTTTCATAC TGAGGGAGTG CACAGCTCTT CTGTGCTGAG TAGCTAACTG     180

TCAGAAAGTA TCCTCAGTTT TGTCTTCATT CCTTAAATAA AATTCTGAAG GAAAAACAAA     240

AACAAAAAAC CCTTCAATTT GAAATTTACT GTAAATGCTT TTTTACTTTG AATTGAAATA     300

GTATCTTCAA ATTGGTAGAA ATCTTTTCAG GTGACAGTTG ATATTTGAAA GGATTGTTTT     360

TATCAGACTC AATTCTAATC TCTTCTCGTT GAGTAATGCT GGTTAGCTGT TAAGGTGGCG     420

TGTTGCAGTG CAGAGTGCTT GGCTGTTTCC TGTTTTCTCC TGATTGCTCC TGTGTAACGA     480

TGCCTTGTCG TGCAGAAACA AATGGCTGTC CAGTTAATTA AAATGCCTGA CAACTGCACT     540

TCCAATCACC CGGGCCTTGC ATAAAAATAA CGGAGCATAC AGTGAGCACA TCTAGCTGAT     600

GGTATACACA CCTTATTTTT TCCAGAATGG TAAATCTTGC CAACATGCAT ATATGAACTT     660

ATATTTGAGA AATGTAATCT TAAGAAAGAA ATGGTTCATT CCTCTGTAAG TACTGATTGG     720

TGTATCTTTT GCTTAAGACA TCTTGTACTA TACCCACTGT CTCTGTAGGT TAATATTAAA     780

CATTTTTTCT GTGTTTTAAC TTTTCTCAAC TTAATGTCTG AGTCAGCTTA TTTTTAGCTG     840

AAAGATTTCT GCAATATACC TGTCAATGTT TAACTTCTAT ATAGGTAACA GAATGCATTC     900

TACTGCTTCT TAACTTTAGN NCTGGGGTTG CCTTTTAAAT TACTCTGGGG CGA            953
```

METHOD FOR SEQUENCING NUCLEIC ACIDS

DESCRIPTION

The present invention concerns a method for the non-radioactive sequencing of nucleic acids.

In general two methods are known for DNA sequencing, namely the chemical degradation method according to Maxam and Gilbert (A. M. Maxam and W. Gilbert, Proc. Natl. Acad. Sci. USA 74 (1977), 560 and A. M. Maxam and W. Gilbert, Methods in Enzymol. 65 (1980), 499) and the enzymatic chain termination method (F. Sanger et al., Proc. Natl. Acad. Sci. USA 74 (1977), 5463–5467).

In the Maxam-Gilbert method labelled DNA molecules are modified chemically in a base-specific manner, a partial chain termination is effected and the fragments obtained in this way are separated according to size and the sequence is determined by means of the labelling.

In the method according to Sanger many labelled nucleic acid fragments are produced of different length starting from a DNA template by enzymatic elongation or extension of a synthetic oligonucleotide primer with the aid of polymerase and a mixture of deoxyribonucleoside triphosphates and chain terminating molecules, in particular dideoxyribonucleoside triphosphates. In this procedure a mixture of a particular deoxyribonucleoside triphosphate (dNTP) and a corresponding dideoxyribonucleoside triphosphate (ddNTP) is usually used together with the three other deoxyribonucleoside triphosphates in each of four mixtures. In this manner a statistical incorporation of the chain terminating molecules into the growing nucleic acid chain is achieved, but after incorporation of the chain terminating molecule the DNA chain cannot grow further because of the absence of a free 3'-OH group. Thus numerous DNA fragments of different length are formed which from a statistical point of view contain at least one chain terminating molecule at each possible incorporation site and end there. These four mixtures each having fragments ending specifically at a base due to the incorporation of chain terminating molecules are separated according to their length, e.g. by polyacrylamide gel electrophoresis, usually in four different lanes and the sequence is determined by means of a labelling of these nucleic acid fragments.

Up to about 1986 the DNA sequencing was carried out using radioactive ($^{32}$p or $^{35}$S) labels. The gelelectrophoretic separation of the fragments and autoradiography of the nucleotide sequence was carried out either manually or semi-automatically. Today DNA sequencing is carried out with automated systems in which a non-radioactive label, in particular a fluorescent label is used (L. M. Smith et al., Nature 321 (1986), 674–679; W. Ansorge et al., J. Biochem. Biophys. Meth. 13 (1986), 315–323). In these automated systems the nucleotide sequence is read directly during the separation of the labelled fragments and entered straight into a computer.

At present two different non-radioactive labelling systems are available for DNA sequencing according to the chain termination method. One possibility of labelling nucleic acid fragments is to use a labelled oligonucleotide primer for the extension reaction so that the nucleic acid chain carries a label at its 5' end. The other possibility is to use labelled terminators ie. chain terminating molecules so that the nucleic acid chain carries a label at its 3' end. A paper by Prober et al. (Science 238 (1987), 336–341) describes a sequencing method in which the four chain-terminating ddNTPs are each coupled to different fluorescent dyes so that all four sequencing mixtures can be separated on a single gel lane. A similar system using four different labelled primers is disclosed in GB-A 2155176.

However, in both the aforementioned methods only a single label is introduced into the nucleic acid chain to be determined which can often lead to sensitivity problems. A further disadvantage in the use of dye-labelled oligonucleotide primers, in particular in a "walking primer strategy" is that different primers have to be used for each sequencing reaction, the production of labelled primers, however, being very expensive or/and complicated. Moreover the hybridization of a primer with the nucleic acid template is sometimes hindered by the use of labelled primers which can lead to inaccurate sequencing results.

The use of dye-labelled terminators, in particular dideoxyribonucleoside triphosphates, has also proven to be unsatisfactory. These labelled terminators are only accepted poorly by the polymerase as substrates so that they have to be added to the reaction mixture in a large concentration (millimolar range) and in a highly purified form (quantitative separation of unlabelled molecules). As a consequence the use of labelled terminators is very expensive. Moreover worse results are obtained than for example when using labelled primers.

Thus the object of the present invention was to provide a method for sequencing nucleic acids in which the disadvantages of the state of the art are at least partially eliminated.

The object according to the invention is achieved by a method for sequencing nucleic acids by (a) producing a mixture of labelled nucleic acid fragments of different length, (b) separating the labelled nucleic acid fragments according to size and (c) determining the nucleic acid sequence via the labelling of the individual fragments, which is characterized in that nucleic acid fragments are determined which are labelled by incorporation of deoxyribonucleoside triphosphates with a non-radioactive labelling group.

The sequencing according to the method of the invention can be carried out by the chemical degradation method according to Maxam and Gilbert as well as by the enzymatic chain termination method according to Sanger. In both cases one obtains a mixture of non-radioactively labelled nucleic acid fragments of different length which contain at least one deoxyribonucleoside triphosphate as an "inner label" which is provided with a radioactive labelling group. It is generally found that the method according to the invention can be applied in a simple manner in all known DNA sequencing protocols (e.g. also in solid phase sequencings).

Suitable non-radioactive labelling groups are for example metals, magnetic labelling groups which are detectable by nuclear resonance or by a superconducting quantum-interferometric detector (SQUID), phosphorescent or fluorescent dyes. Fluorescent dyes such as rhodamine, Texas red, phycoerythrin or fluorescein and its derivatives are particularly preferred. In particular those fluorescent dyes are preferred which exhibit an absorbance in a range of 600 to 800 nm. Examples of numerous suitable dyes may be found in the catalogue of the Molecular Probes Company.

In the labelled deoxyribonucleoside triphosphates the label is preferably coupled via a linker to the $C_5$ position of pyrimidine bases (uracil, thymine or cytosine) or to the $N_7$ or $C_8$ position of purine bases (adenine, guanosine, hypoxanthine) or to the $C_7$ position of purine bases (7-deazaguanidine). The number of atoms in the chain of the linker is usually 1 to 50, preferably 4 to 24 and particularly preferably 10 to 18.

The use of labelled dNTPs has already been proposed in DE-OS 38 41 565 as being desirable. However, at that time neither suitable chemical substances were available nor was it known whether these substances would prove to be suitable substrates in the sequencing reaction in particular in an automated sequencing reaction.

Surprisingly fluorescein-labelled dUTP (fluorescein-12-2'-deoxyuridine-5'-triphosphate or fluorescein-12-dUTP) which is commercially available from Boehringer Mannheim (Catalogue No. 1373242) has proven to be particularly suitable Fluorescein-12-dUTP can be used instead of dTTP or together with dTTP in the method according to the invention. In addition fluorescein-12-2'-dCTP, fluorescein-15-2'-dGTP and in particular fluorescein-15-2'-dATP have also proven to be excellently suitable labelled dNTPs.

In the method according to the invention it is possible to use a single labelled dNTP or also several labelled dNTPs concurrently in one mixture By using several labelled dNTPs simultaneously it is possible to greatly increase the number of labelled nucleotides in a chain, which is for example advantageous when the starting material to be sequenced is only available in a very small concentration.

If the method according to the invention is carried out according to the chemical degradation method of Maxam and Gilbert then there are various ways of introducing the label into the nucleic acid to be sequenced.

On the one hand the label can for instance be introduced by means of enzymatic extension of an oligonucleotide primer in the presence of a polymerase, the nucleic acid to be sequenced as a template and all four deoxyribonucleoside triphosphates of which at least one contains a labelling group. In this process a complementary strand to the nucleic acid to be sequenced is formed by elongation of the primer which carries labelling groups and which can be subsequently sequenced in the usual manner ide. by partial base-specific cleavage by means of chemical methods and subsequent separation of the resulting fragment mixture.

In a further preferred method of labelling the nucleic acids, an oligonucleotide cassette which contains at least one labelled deoxyribonucleotide is ligated into restriction fragments of the nucleic acid to be sequenced with 5' or 3' protruding ends.

In yet a further preferred embodiment for labelling nucleic acids, restriction fragments of the nucleic acid to be sequences which have protruding 5' ends are filled up with polymerase or reverse transcriptase in the presence of at least one labelled deoxyribonucleoside triphosphate.

Examples of further preferred embodiments of the Maxam-Gilbert method are disclosed in DE-OS 38 39 397 the contents of which are referred to here.

The sequencing according to the invention is preferably carried out by the enzymatic chain termination method according to Sanger. Preferred is a method for the non-radioactive sequencing of nucleic acids by (a) enzymatic extension of an oligonucleotide primer in the presence of polymerase, deoxyribonucleoside triphosphates, chain terminating molecules and the nucleic acid to be sequenced as a template in one or several mixtures in which a mixture of labelled nucleic acid fragments of different length is formed, (b) separation of the labelled nucleic acid fragments according to size and (c) determination of the nucleic acid sequence by means of the labelling of the individual fragments, which is characterized in that the elongation of the oligonucleotide primer is carried out in the presence of at least one deoxyribonucleoside triphosphate with a non-radioactive labelling group.

It surprisingly was found that non-radioactively labelled deoxyribonucleoside triphosphates, in particular deoxyribonucleoside triphosphates labelled with fluorescent dyes, are accepted as the substrate to an adequate extent by the polymerase in a sequencing reaction. Excellent results were obtained on an automatic DNA sequencing instrument (A.L.F. DNA Sequencer from Pharmacia LKB) when using fluorescein-12-dUTP, fluorescein-12-dCTP, fluorescein-15-dATP and fluorescein-15-dGTP as the non-radioactively labelled deoxyribonucleoside triphosphates and in each case the other non-labelled deoxyribonucleoside triphosphates.

In contrast to methods according to the state of the art, several labelled nucleotides can be incorporated simultaneously into a single DNA fragment in the method according to the invention thus increasing the signal strength and consequently the sensitivity of the determination by an order of magnitude or more.

In addition the high signal strength enables a sensitive detection of fluorescent bands in an automatic sequencing instrument even when they migrate very rapidly through the laser ray used as a detector so that this enables the performance of DNA sequencing reactions which work at a very high speed—up to several thousand bases per hour per clone—by use of high voltages e g. in ultrathin plate gels or in ultrathin capillaries.

An advantage of the method according to the invention is its simplicity since no labelled primers and no labelled chain terminating molecules are necessary. This is of particular importance for sequencing projects on a large scale such as the sequencing of the human genome or other genome projects. When labelled dNTPs are used in the sequencing reaction, standard primers can be used so that it is possible to avoid a time-consuming or/and expensive production of labelled oligonucleotide primers. On the other hand if it is desired it is of course also possible to use labelled primers.

A further advantage of the method according to the invention is that the resolution of the sequence ladder, in particular when it is of great length, is surprisingly improved compared to the known use of labelled primers from the state of the art. This applies in particular to a procedure in which the labelling and the extension are carried out in two separate steps (see examples 2 and 3) and when using fluorescein-dATP or fluorescein-dUTP as the label.

A distinguishing feature of the method according to the invention is that one can use an oligonucleotide primer without a labelling group in particular an oligo-nucleotide primer unmodified at the 5' end. On the other hand it is, however, also possible to use an oligonucleotide primer which is modified at its 5' end with a dye or/and a group capable of affinity binding in combination with the labelled dNTPs. Thus a double labelling is for example possible i.e. one uses a dye-labelled oligonucleotide primer which has a fluorescence wavelength which is different to that of the labelled dNTPs used in the corresponding mixture. In addition the oligonucleotide primer can be biotinylated at its 5' end which for example allows binding to a solid phase coated with streptavidin. Other examples of groups which are capable of affinity binding are haptens (e.g. digoxigenin or digoxin) which are capable of binding to a specific antibody for the corresponding hapten.

It is expedient to use deoxyribonucleoside triphosphates as chain terminating molecules for the method according to the invention which are modified at the 3' position of the deoxyribose in such a way that they have no free OH groups but are nevertheless accepted by the polymerase as a substrate. Examples of such chain terminating molecules are for instance 3'-fluoro-, 3'-O-alkyl- or 3'-H-modified deoxyribonucleotides. 3'-H-modified deoxyribonucleotidese i e. dideoxyribonucleoside triphosphates (ddNTPs), are preferably used as chain terminating molecules. In the method according to the invention it is preferable to use unlabelled chain terminating molecules however, it is also possible to use labelled chain terminating molecules such as those known to one skilled in the art.

According to the invention the Klenow fragment of *E. coli* DNA polymerase I, modified or unmodified T7 DNA polymerasee T4 DNA polymerase, Taq DNA polymerasee Bst DNA polymerase or reverse transcriptase are preferably used for the enzymatic extension of an oligonucleotide primer or for filling up restriction fragments. Of these polymerasese T7 DNA polymerase and the thermostable Taq and Bst DNA polymerases are particularly preferred. Surprisingly the non-radioactively labelled dNTPs are accepted by these enzymes as substrates in a sequencing reaction.

In the method according to the invention the separation of the labelled nucleic acid fragments can be carried out according to all methods known in the art e g. by various electrophoretic (e.g. polyacrylamide gel electrophoresis) or chromatographic (e.g. HPLC) techniques, a gel electrophoretic separation being preferred. In addition the separation of the labelled nucleic acids can be carried out in any desired manner i.e. manually, semi-automatically or automatically, however, the use of an automatic sequencing instrument is generally preferred. In this case it is then possible to separate. the labelled nucleic acids in ultrathin plate gels of 20 to 200 $\mu$m, preferably 100 $\mu$m thickness (see e.g. Stegemann et al., Methods in Mol. and Cell. Biol. 2 (1991), 182–184) or capillaries.

When using deoxyribonucleoside triphosphates which are labelled with fluorescent dyes, the determination of the label after separation of the individual nucleic acid fragments according to their size can be achieved by exciting the fluorescent dye by a laser or other suitable light sources (e.g. LEDs, fluorescent lamps or diode lasers). Such methods are known to a person skilled in the art and are already used in commercial sequencing instruments (e.g. A.L.F. Sequencer from Pharmacia).

If only a very small amount of the nucleic acid to be sequenced is available for a sequencing determination according to the method of the present invention then an amplification step can be carried out. One possibility of amplification is to carry out one or several cycles of the polymerase chain reaction (PCR) using two primers before the actual sequencing. The PCR is usually carried out without labelled dNTPs. In this way the nucleic acid to be sequenced can be amplified before carrying out the actual sequencing.

On the other hand the amplification step can also be achieved using a "thermocycling" reaction. The thermocycling reaction corresponds to a "normal" sequencing reaction which, however—like a PCR—is carried out in several cycles. The reaction mixture contains the nucleic acid template, the primer, the dNTPs and in each case corresponding chain terminating molecules as well as a preferably thermostable polymerase. In this way always a certain amount of labelled nucleic acid fragments is synthesized per cycle and large amounts of labelled fragments can be generated in several cycles so that the DNA is linearly amplified and not exponentially as in the PCR.

The nucleic acid to be sequenced may be present in a single-stranded as well as in a double-stranded form. Good results are obtained when the nucleic acid to be sequenced is located on a double-stranded DNA vector e.g. a plasmid, cosmid, bacteriophages (lambda or P1), a viral vector or an artificial chromosome (artificial yeast chromosome).

In a first preferred embodiment of the method according to the invention the enzymatic elongation reaction is carried out in the usual manner i.e. in several separate mixtures in which different chain terminating molecules are used in each preparation i.e. terminators with different nucleotide bases. The chain terminating molecules can either be added right at the beginning of the reaction or the reaction can be carried out in two steps, an extension step in the absence of chain terminating molecules and a termination step in the presence of the respective chain terminating molecule. If T7 DNA polymerase is used for the chain elongation, the extension step (without ddNTPs) can for example be carried out in the presence of magnesium ions and the termination step (with ddNTPs) can be carried out in the presence of manganese ions.

According to this embodiment four parallel mixtures are preferably carried out in which a different ddNTP is present in each mixture as the chain terminating molecule. If the same labels (one or several labelled dNTPs) are used in each of these four mixtures, a separate separation of the individual mixtures is necessary. In a preferred variant of this embodiment one can carry out two (or several) sequencing reactions using differently labelled dNTPs in which in each case those labelling groups are used which can be detected concurrently. Thus for example one can use fluorescein-dNTP in a first reaction (i.e. in all four mixtures of this reaction) and rhodamine-dNTP in a second reaction. The evaluation of these two reactions can be carried out jointly by applying two mixtures each with different labels (i.e. a fluorescein and a rhodamine label) onto a single gel lane and determining them separately (by measurement at different fluorescent wavelengths).

If on the other hand different labels are used for each single reaction in different mixtures (e.g. by using fluorescent dyes with different absorption wavelengths) then it is also possible to jointly separate several or even all mixtures of a single reaction e.g. on one gel lane.

Another preferred embodiment of the method according to the invention comprises using at least two different chain terminating molecules in different amounts in a single mixtures it being possible in this case to differentiate the fragments by means of the intensity of the signal of their label. Such methods are for example the subject matter of DE-OS 38 41 565.

The present invention in addition concerns the use of non-radioactively labelled deoxyribonucleoside triphosphates in methods for sequencing nucleic acids according to the degradation method of Maxam and Gilbert or according to the chain termination method of Sanger. In this case the label is preferably a fluorescent dye, particularly preferably fluorescein or a derivative thereof. The label is preferably coupled to the dNTP via a linker. The number of atoms in the chain of the linker is generally 1 to 50, preferably 4 to 24 and particularly preferably 8 to 18. The use of fluorescein-12-dUTP, fluorescein-12-dCTP, fluorescein-15-dGTP or/and fluorescein-dATP has proven to be advantageous for an automatic sequencing method.

The invention also in addition concerns a reagent for sequencing nucleic acids which contains at least one deoxyribonucleoside triphosphate which is labelled with a non-radioactive labelling group. The reagent can for example be in the form of a solutions a suspension or a lyophilisate. The reagent can also be a component of a reagent kit for sequencing nucleic acids and this kit can also contain additional reagents (e.g. enzyme, primers, buffer solutions, non-labelled NTPs, terminators).

It is intended to further elucidate the invention by the following examples in conjunction with FIGS. 1 to 3.

EXAMPLE 1

DNA sequencing using a fluorescein-12-dUTP label

Figure 1:
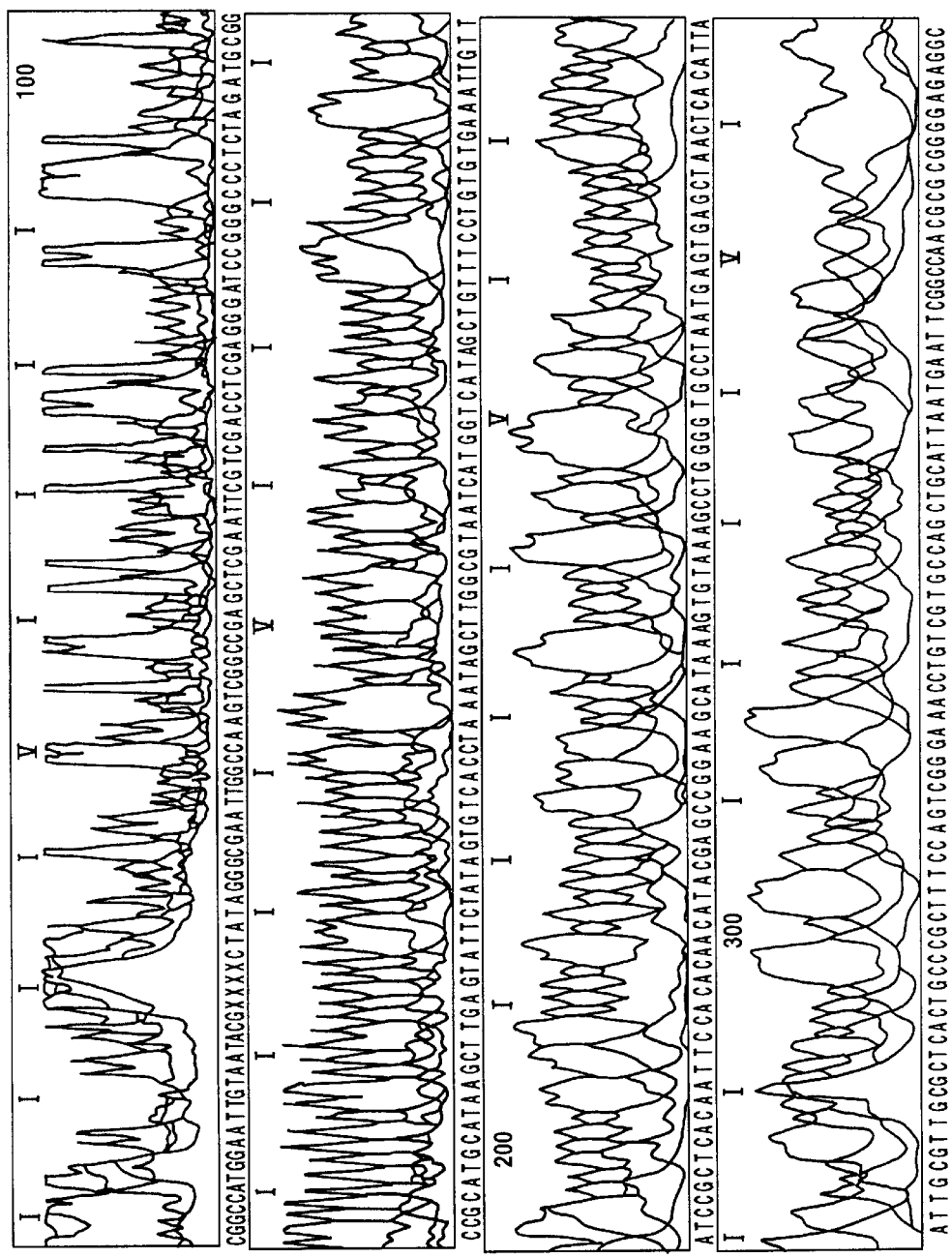
FIG. 1 shows the result of a plasmid sequencing SEQ ID NO: 1 using fluorescein-12-dUTP as the label.

The sequencing was carried out using an automatic DNA sequencing instrument (A.L.F. DNA Sequencer from Pharmacia LKB). Experiments were carried out with T7 DNA polymerase and manganese or magnesium buffer using single-stranded and double-stranded DNA templates. The nucleotides and enzymes were obtained from Pharmacia PL. Fluorescein-12-dUTP was obtained from Boehringer Mannheim. Good results were obtained using the following reaction protocol:

1. Denaturation and annealing

5 µg plasmid-DNA (prepared by purification over a Qiagen column) in 6 µl redistilled $H_2O$ was mixed with 2 µl sequencing primer (1 µmol/l), denatured by addition of 1 µl 1 M NaOH for 3 minutes at 70° C. and neutralized with 1 µl 1 M HCl. 2 µl freshly prepared 10× reaction buffer (300 mmol/l Tris HCl, pH 7.5, 150 mmol/l DTT, 60 mmol/l $MnCl_2$, 460 mmol/l DL-isocitrate) was added and incubated for 15 minutes at 37° C.

2. Extension and labelling

2 µl labelling mixture (in each case 1.5 µmol/l dATP, dCTP, dGTP and fluorescein-12-dUTP) was added together with 3.5 U T7 DNA polymerase to the above mixture and incubated for 10 minutes at room temperature.

3. Termination

4 µl aliquots of the reaction product were added to 3 µl of the four respective termination mixtures (1 mmol/l dATP, 1 mmol/l dCTP, 1 mmol/l 7-deaza-dGTP, 1 mmol/l dTTP, in each case 5 µmol/l ddNTP) and incubated for 5 minutes at 37° C. The reactions were stopped with 4 µl deionized formamide containing 5 mg/ml dextran blue, denatured by heating and applied to the sequence gel.

FIG. 1 shows the result of a typical plasmid sequencing using fluorescein-12-dUTP as the label. The signal starts directly after the first labelled T residue after the priming site without visible primer peak. The intensities in the case of multiple peaks are the same as in primer experiments with end labelling. Magnesium as well as manganese buffer have proven to be suitable for the T7 DNA polymerase.

An automated DNA sequencing using fluorescent-labelled dNTPs has various advantages compared to other labelling techniques.

1. The labelling intensity is significantly stronger than with known protocols. In this case 200 ng ss-DNA are adequate for sequencing. Ca. 1 µg ss-DNA is usually used in known methods.
2. Any desired unlabelled oligonucleotide primer (e.g. primers for expression vectors) can be used directly. The "walking primer" method is facilitated since it is not necessary to label the primers or purify the labelled product. Since no interaction can occur with a dye at the 5' end of the primer, shorter oligonucleotides (12–15 bases) are suitable for use.
3. The price of the labelling is negligible (less than 0.05 DM per reaction) compared to fluorescent-labelled ddNTPs. Moreover it is not necessary to remove non-incorporated label
4. The fluorescent-labelled dUTP is accepted as a substrate by many DNA polymerases (T4, T7, Klenow, Taq Bst, AMV reverse transcriptase)

EXAMPLE 2

Single-stranded DNA sequencing with fluorescein-dNTPs using the Pharmacia AutoRead Kit 1. Denaturing and annealing (in one vessel)

10 µl single-stranded template DNA (200 ng M13) 2 µl unlabelled sequencing primer (5 µmol/l) and 2 µl annealing buffer were mixed, heated for 3 minutes to 65° C. and allowed to cool to 37° C.

2. Labelling

1 µl labelling mixture (10 µmol/l labelled dNTP and 1 µmol/l of the unlabelled dNTPs in each case) was added together with 0.5 µl T7 DNA polymerase (3.5 U) to the above mixture, mixed and incubated for 10 minutes at 37° C.

3. Termination

The above mixture was mixed with 1 µl extension buffer. Then 4 µl aliquots of this were added to 4 µl of the respective A, C, G and T mixes (3 µl of the respective termination mixture and 1 µl DMSO) and incubated for 5 minutes at 37° C. The reactions were stopped in each case with 4 µl stop solution. The mixtures were subsequently denatured by heating and applied to the sequence gel.

EXAMPLE 3

Double-stranded DNA sequencing with fluorescein-dNTPs using the Pharmacia AutoRead Kit 1. Denaturing and annealing (in one vessel)

10 µl plasmid DNA (⅓ of a minipreparation over a Quiagen column), 2 µl non-labelled sequencing primer (5 µmol/l) and 1 µl 1 mol/l NaOH were mixed, heated for 3 minutes at 65° C. and incubated at 37° C.

2. Labelling

1 µl 1 mol/l HCl, 2 µl annealing buffer, 1 µl labelling mixture (10 µmol/l labelled dNTP and 1 µmol/l of non-labelled dNTPs in each case) were added together with 0.5 µl T7 DNA polymerase (3.5 U) to the above mixture and incubated for 10 minutes at 37° C.

3. Termination

The above mixture was mixed with 1 µl extension buffer. 4 µl aliquots of this were added to 4 µl of the respective A, C, G and T mixes (3 µl of the respective termination mixtures and 1 µl DMSO) and incubated for 5 minutes at 37° C. The reactions were stopped with 4 µl stop solution. The mixture was subsequently denatured by heating and applied to the sequence gel.

Figure 2:
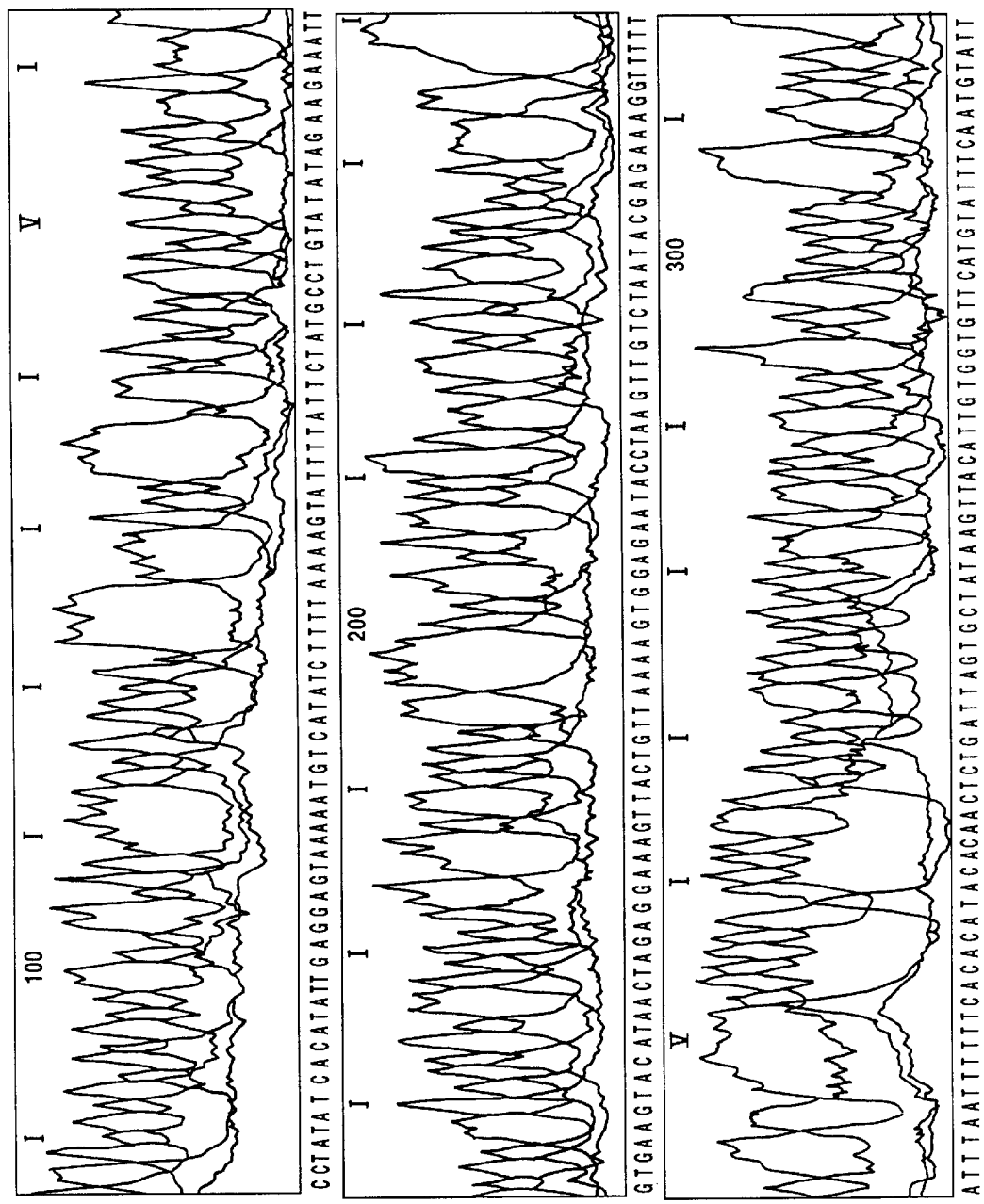
FIG. 2 shows the result of a plasmid sequencing SEQ ID NO: 1 using fluorescein-12-dCTP as the label.
Figure 3A:
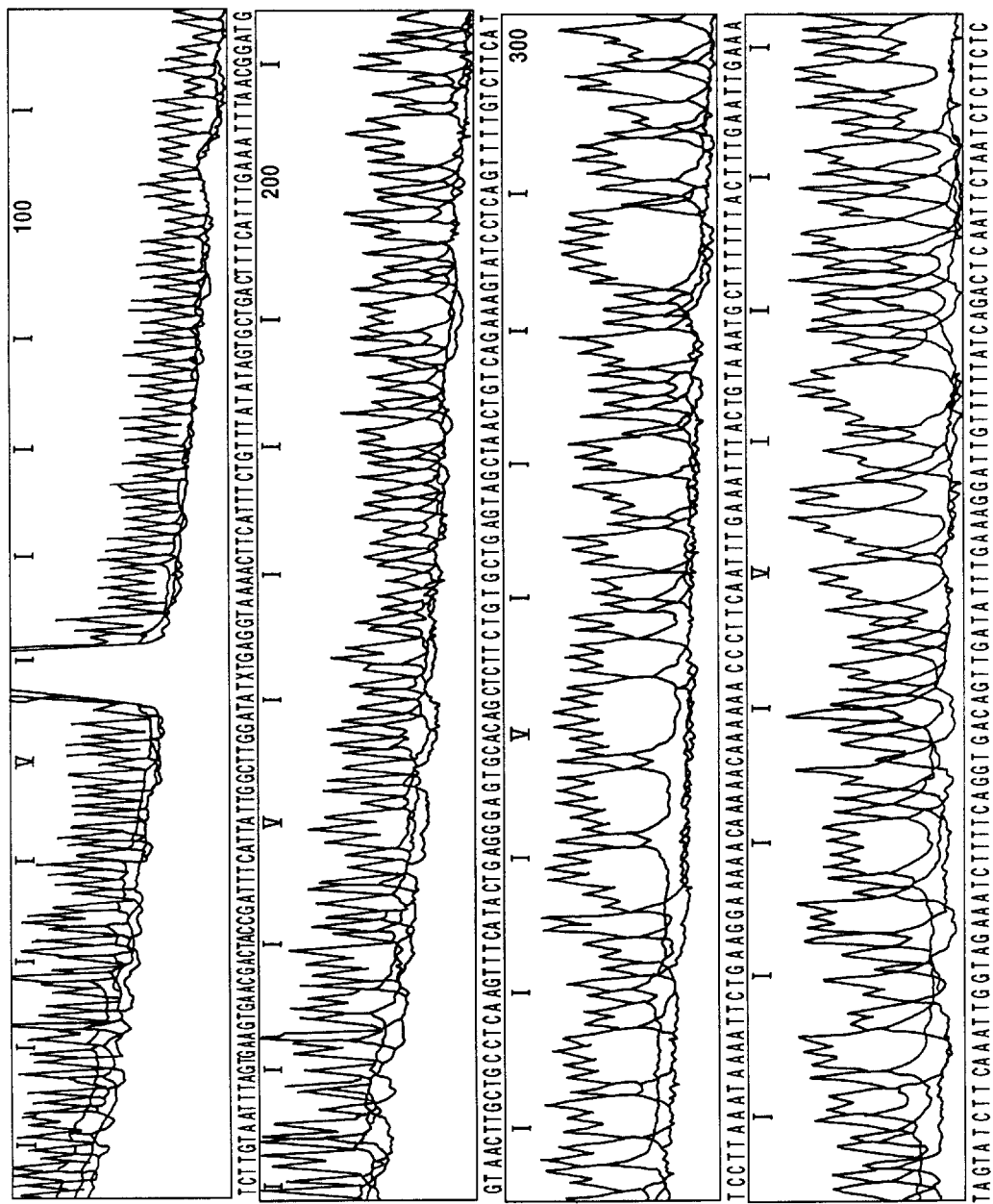
FIGS. 3a, 3b, and 3c show the result of a plasmid sequencing SEQ ID NO: 3 using fluorescein-15-dATP as the label.
Figure 3B:
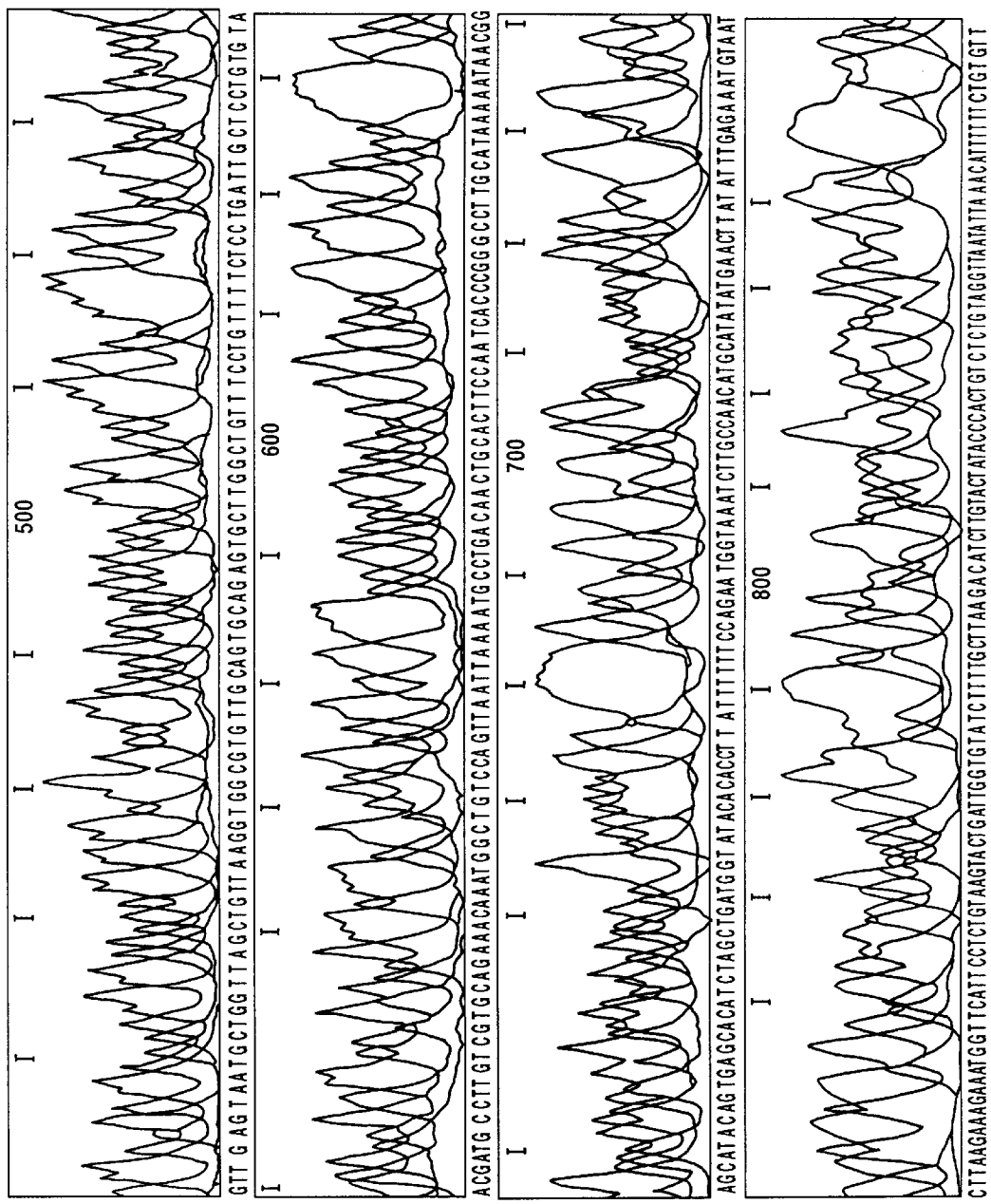
Figure 3C:
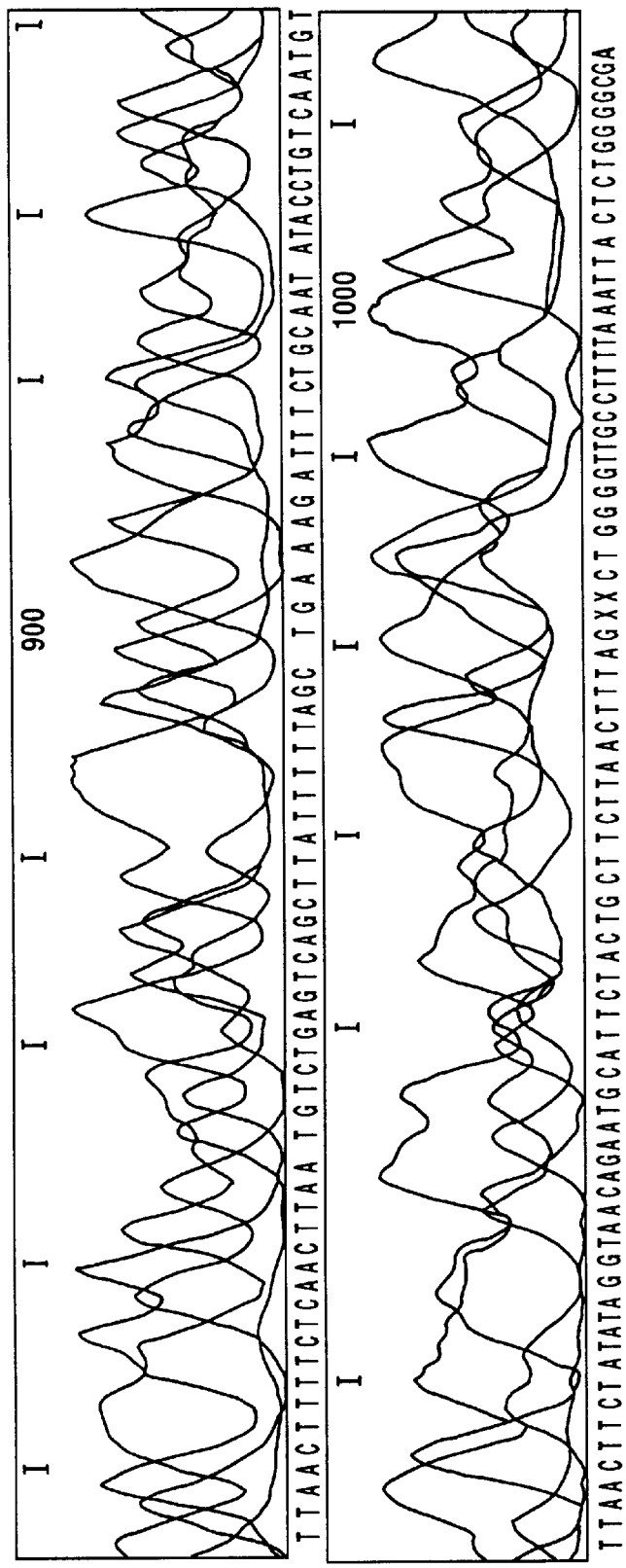

FIGS. 2 and 3 show the results of a plasmid sequencing using the above protocol and fluorescein-12-dCTP (FIG. 2) or fluorescein-15-dATP (FIG. 3) as the label The analysis of the sequence gels was carried out on an automated EMBL Fluorescence Sequencer. When using fluorescein-15-dATP as the label it is possible to read up to 1000 bases.

We claim:

1. A method for sequencing nucleic acids, comprising the steps of
(a) producing a mixture of labelled nucleic acid fragments of different length from a template nucleic acid by enzymatic extension of an oligonuclectide primer, wherein at least one deoxyribonucleotide triphosphate with a non-radioactive labelling group is incorporated as an inner label in the absence of chain termination molecules,
(b) adding chain errnination molecules after the labeled nucleic acid fragments are produced to terminate said enzymatic extension,
(c) separating the labelled nucleic acid fragments according to size, and
(d) determining the nucleic acid sequence by means of the labelling of the separated fragments, wherein said chain termination molecules are 3' modified deoxyribonucleotide triphosphates.

2. The method according to claim 1, wherein the mixture of labelled nucleic acid fragments is produced by the enzymatic chain termination method.

3. The method according to claim 2, wherein the mixture of labelled nucleic acid fragments is produced by enzymatically extending an oligonucleotide primer in the presence of polymerase, deoxyribonucleotide triphosphates and the template nucleic acid to form a mixture of labelled nucleic acid fragments of different length, and
wherein at least one deoxyribonucleotide triphosphate is labeled with a non-radioactive labelling group.

4. The method according to claim 1, wherein said deoxyribonucleoside triphosphate is linked via a linker to the non-radioactive labelling group.

5. The method according to claim 4, wherein the number of atoms in the linker is 10 to 18.

6. The method according to claim 1, wherein said deoxyribonucleoside triphosphate is labelled with a fluorescent dye.

7. The method according to claim 6, wherein said fluorescent dye is fluorescein or derivatives thereof.

8. The method according to claim 7, wherein said fluorescein or derivatives thereof is selected from the group consisting of fluorescein-12-dUTP, fluorescein-12-dCTP, fluorescein-15-dGTP and fluorescein-15-dATP.

9. The-method according to claim 1, wherein said labelled nucleic acid fragments are separated by gel electrophoresis.

10. The method according to claim 1, wherein the separation of the labelled nucleic acid fragments is carried out in an automatic sequencing instrument.

11. The method according to claim 9, wherein the separation is carried out in ultrathin plate gels or capillaries.

12. The method according to claim 1, wherein said deoxyribonucleotide triphosphates are labelled with fluorescent dyes, and after separating the nucleic acid fragments the fluorescent dye is excited by laser in order to determine the label.

13. The method according to claim 1, further comprising carrying out at least one cycle of a PCR reaction prior to step a), to amplify the amount of the nucleic acid to be sequenced.

14. The method according to claim 2, wherein step a) is repeated at least once as a thermocycling reaction to amplify the amount of labelled nucleic acid fragments.

15. The method according to claim 1, wherein the template nucleic acid is located on a double-stranded DNA vector.

16. The method according to claim 15, wherein the double-stranded DNA vector is selected from the group consisting of a plasmid, cosmid, bacteriophage, viral vector and, an artificial chromosome.

17. The method according to claim 2, wherein the enzymatic extension in the chain termination is carried out in several separate mixtures in which a different chain terminating molecule is used in each mixture.

18. The method according to claim 17, wherein the same label is used in all mixtures so that a separate separation of the individual mixtures is necessary.

19. The method according to claim 17, wherein different labels are used in different mixtures so that a joint separation of the mixtures is possible.

* * * * *